(12) United States Patent
David et al.

(10) Patent No.: US 8,041,004 B2
(45) Date of Patent: Oct. 18, 2011

(54) X-RAY INTERFEROMETER FOR PHASE CONTRAST IMAGING

(75) Inventors: Christian David, Lauchringen (DE); Franz Pfeiffer, Brugg (CH)

(73) Assignee: Paul Scherrer Institut, Villigen PSI (CH)

( * ) Notice: Subject to any disclaimer, the term of this patent is extended or adjusted under 35 U.S.C. 154(b) by 362 days.

(21) Appl. No.: 12/373,317

(22) PCT Filed: Jun. 28, 2007

(86) PCT No.: PCT/EP2007/005728
§ 371 (c)(1),
(2), (4) Date: Jan. 12, 2009

(87) PCT Pub. No.: WO2008/006470
PCT Pub. Date: Jan. 17, 2008

(65) Prior Publication Data
US 2009/0316857 A1    Dec. 24, 2009

(30) Foreign Application Priority Data

Jul. 12, 2006 (EP) ..................... 06014449
Sep. 12, 2006 (EP) ..................... 06019022

(51) Int. Cl.
*G03H 5/00* (2006.01)
(52) U.S. Cl. ........................................ 378/36
(58) Field of Classification Search ............. 378/36
See application file for complete search history.

(56) References Cited

U.S. PATENT DOCUMENTS

| 3,944,833 A * | 3/1976 | Hounsfield ............... 250/367 |
| 2006/0039532 A1 | 2/2006 | Wu et al. |
| 2009/0092227 A1 | 4/2009 | David et al. |

FOREIGN PATENT DOCUMENTS

| EP | 1447046 A1 | 8/2004 |
| EP | 1731099 A1 | 12/2006 |

OTHER PUBLICATIONS

Pfeiffer et al: "Phase Retrieval and Differential Phase-Contrast Imaging with Low-Brilliance X-Ray Sources", XP002422783, Nature Physics, Nature Publishing Group, Mar. 26, 2006, pp. 258-261, London, GB.
Weitkamp et al: "X-Ray Phase Imaging with a Grating Interferometer", XP002397629, Optics Express, Optical Society of America, Aug. 8, 2005, pp. 6296-6304, vol. 13, No. 16, Washington, DC.
Momose et al: "Phase Tomography by X-Ray Talbot Interferometry for Biological Imaging", XP002444795, Japanese Journal of Applied Physics, Jun. 2006, pp. 5254-5262, vol. 45, No. 6A.

* cited by examiner

*Primary Examiner* — Hoon Song
*Assistant Examiner* — Mona M Sanei
(74) *Attorney, Agent, or Firm* — Laurence A. Greenberg; Werner H. Stemer; Ralph E. Locher (57) ABSTRACT

An interferometer for x-rays, in particular hard x-rays, for obtaining quantitative x-ray images from an object, includes: a) an x-ray source, preferably a standard polychromatic x-ray source, b) a diffractive beam splitter grating other than a Bragg crystal, preferably in transmission geometry, c) a position-sensitive detector with spatially modulated detection sensitivity having a number of individual pixels; d) means for recording the images of the detector in a phase-stepping approach; and e) means for evaluating the intensities for each pixel in a series of images in order to identify the characteristic of the object for each individual pixel as an absorption dominated pixel and/or an differential phase contrast dominated pixel and/or an x-ray scattering dominated pixel.

16 Claims, 4 Drawing Sheets

X-RAY INTERFEROMETER FOR PHASE CONTRAST IMAGING

BACKGROUND OF THE INVENTION

Field of the Invention

The present invention relates to an interferometer for x-rays, in particular hard x-rays, for obtaining quantitative x-ray images from an object.

In conventional x-ray imaging, contrast is obtained through the differences in the absorption cross section of the constituents of the object. The technique yields excellent results where highly absorbing structures, e.g., bones, are embedded in a matrix of relatively weakly absorbing material, e.g., the surrounding tissue of the human body. However, in those cases where different forms of tissue with similar absorption cross-sections are under investigation (e.g., mammography or angiography), the x-ray absorption contrast is relatively poor. Consequently, differentiating pathologic from non-pathologic tissue from an absorption radiograph obtained with a current hospital-based x-ray system still remains practically impossible for certain tissue compositions.

To overcome these limitations, several methods to generate radiographic contrast from the phase shift of x-rays passing through the sample have been investigated in the past, mostly using radiation from highly brilliant synchrotron sources. As an alternative approach, the European Patent application 05 012 121 proposes a grating based hard x-ray interferometer that can efficiently be used to retrieve quantitative phase images with conventional polychromatic x-ray sources of essentially no spatial coherence. The results of our work on the principles and experimental demonstrations of grating interferometry have been discussed in this European patent application No. 05 012 121.

The setup according to the above mentioned European patent application comprises a source grating, a beam splitter grating and an analyzer absorption grating. The source grating designed as an absorbing mask with transmitting slits, typically placed close to x-ray source, creates an array of individually coherent, but mutually incoherent sources. Each individual line source provides enough spatial coherence for the differential phase contrast (DPC) image formation process. Since the source mask can contain a large number of individual lines, each creating a virtual source, efficient use can be made of large, and correspondingly powerful, sources of more than a few square millimeters. To ensure that each of the line sources contributes constructively to the image formation process, the geometry of the setup should satisfy the condition: $p_0 = p_2\, l/d$, where $p_0$ ($p_2$) is the period of G0 (G2), l the distance between G0 and G1, and d the distance between G1 and G2. It is important to note that the total source size w only determines the final imaging resolution, which is given by wd/l. The arrayed source thus decouples spatial resolution from spatial coherence. The DPC image formation process achieved by the two gratings and is similar to Schlieren imaging or to a Shack-Hartmann wave front sensor. The second grating acts as a beam splitter and divides the incoming beam essentially into the two first diffraction orders. Since the wavelength $\lambda$ of the x-ray radiation ($\sim 10^{-10}$ m) is much smaller than the grating pitch ($\sim 10^{-6}$ m), the angle between the two diffracted beams is so small that they overlap almost completely.

Downstream of the beam-splitter grating, the diffracted beams interfere and form linear periodic fringe patterns in planes perpendicular to the optical axis. Neither the period nor the lateral position of these fringes depends on the wavelength of the radiation used. Perturbations of the incident wave front, such as those induced by refraction on a phase object in the beam, lead to local displacement of the fringes.

The fundamental idea of the grating interferometer based imaging method is to detect the local positions of the fringes and determine from these the phase shift induced by the object. However, since the spacing of the interference fringes does not exceed a few microns, an area detector placed in the detection plane will generally not have sufficient resolution to resolve the fringes, let alone the exact position of their maxima. Therefore, a grating G2 with absorbing lines and the same periodicity and orientation as the fringes is placed in the detection plane, immediately in front of the detector. This analyzer grating acts as a transmission mask for the detector and transforms local fringe position into signal intensity variation. The detected signal profile thus contains quantitative information about the phase gradient of the object.

Unfortunately, the set-up disclosed in said European Patent application does not allow to expand the evaluation of the measured intensities beyond the absorption and phase-contrast characteristics of the investigated object. Further, the existing set-up allows to capture the intensities in a phase-stepping approach merely by stopping the movement the object for the time needed for the phase stepping scan which is, for example, in airport security applications, like scanning the passenger' luggage on a conveyor, not possible.

BRIEF SUMMARY OF THE INVENTION

It is therefore an objective of the invention to expand the opportunities for data interpretation beyond the existing status. It is a further objective to abolish the need for discontinuous movement of the object in intensity acquisition when applying the phase scanning approach.

These objectives are achieved according to the present invention by an interferometer for x-rays, in particular hard x-rays, for obtaining quantitative x-ray images from an object, comprising:
a) an x-ray source, preferably a standard polychromatic x-ray source,
b) a diffractive beam splitter grating other than a Bragg crystal, preferably in transmission geometry,
c) a position-sensitive detector with spatially modulated detection sensitivity having a number of individual pixels;
d) means for recording the images of the detector in a phase-stepping approach; and
e) means for evaluating the intensities for each pixel in a series of images in order to identify the characteristic of the object for each individual pixel as an absorption dominated pixel and/or an differential phase contrast dominated pixel and/or an x-ray scattering dominated pixel.

As an alternate solution for the above-mentioned objectives, an interferometer for x-rays, in particular hard x-rays, for obtaining quantitative x-ray images from an object, preferably including the features of the solution given above, may comprise:
a) a slit mask having a number of slits being arranged between an X-ray source and a beam splitter grating allowing an object to be disposed between the slit mask and the beam splitter grating;
b) at least one analyzer grating being disposed between the beam splitter grating and a detector, wherein the beam splitter grating and each of the at least one analyzer grating having a grating structure associated with the number of slits in the slit mask;

c) the detector is arranged as an array of individual line detectors each having a number of pixels wherein the number of line detectors used corresponds to the number of slits in the slit mask;

d) means for moving the object along a scan direction; said scan direction being oriented perpendicular to the orientation of the gratings in said grating structure;

e) means for recording the images of said detector in a continuous scanning approach; and f) means for evaluating the intensities for each pixel in a series of images representing a phase stepping scan for at least a part of the object moved along the scan direction.

These solutions according to the two alternate interferometers focus on the one hand side on a novel data analysis scheme not only be used to image the absorption and phase-contrast of the object, but also the differences in scattering of the object. For the interpretation of the images gained by the interferometer setup, a much higher accuracy to identify the true structural consistence of the object can be achieved. On the other hand an improved geometry for scanning applications has been found granting now the opportunity to scan an object being moved continuously through the x-ray beam.

A preferred embodiment according to the present invention comprises the means for evaluation the images having calculation means which analyze a course of the detected intensities for each pixel of the detector, wherein a course of the detected intensities is yielded by a predetermined number of images recorded in the phase-stepping approach. Due to the physical behavior of the object the original x-ray radiation is either absorbed, phase shifted and/or scattered, each leaving a distinct footprint in the course of the detected intensities along the scanning direction. Therefore, the calculation means comprises a memory for storing the images gained in the fast stepping approach without an object placed in the beam line since the deviation of the measured intensities with the object in the beam line as compared to the pure image without the object contain more or less the entire useful information.

In order to adapt the detector for matching its sensitivity with the fringe structure of the diffracted x-ray beam, the corresponding spatially modulated detection sensitivity can be generated by an analyzer grating having absorbing lines at the same periodicity and orientation as a set of fringes generate by the diffractive beam splitter grating wherein the analyzer grating is placed in the plane of the detector, preferably immediately in front of the detector.

The phase-stepping approach can be realized on the one hand by the movement of the object. Another realistic alternative can be realized when the phase-stepping approach is achieved by scanning at least one of the gratings relative to the object in a direction substantially perpendicular to the orientation of the lines in the at least one grating.

Another preferred embodiment of the present invention focuses on the exploitation of the gained intensity data and has the intention to visualize the intensities and their portions with respect to their origin in light of the three different physical effects, namely absorption, phase contrast and scattering. This embodiment comprises means for preparing display data for displaying the evaluated images of the object, wherein an encoding approach is used for the differentiation of the individual contribution to each individual pixel, wherein:

a) a value of the differential absorption signal $dA(m,n)/dx$ or the absorption signal $dA(m,n)$ or the absolute value of any of the previous two is assigned to a first codification;

b) a value of the differential phase contrast signal $d\Phi(m,n)/dx$ or the integrated phase signal $\Phi(m,n)$ or the absolute value of any of the previous two is assigned to a second codification;

c) a value of the differential scattering signal $dS(m,n)/dx$ or the scattering signal $S(m,n)$ or the absolute value of any of the previous two is assigned to a third codification.

In further elaborating this approach, the means for preparing display data calculate a superimposed image containing all three absolute values being superimposed according to their respective codification. By superimposing these three individual absolute values for each pixel, a resulting image is generated that reflects the contributions for each pixel. Additionally, the means for preparing display data allow to display for each of the three codifications an individual image, preferably highlighting only those pixels which dominate the respective pixel as compared to the signals in the other two remaining codifications. Therefore, each of said three codifications may comprise an individual signal type, like an individual letter, a symbol and/or a color. One preferred way to implement this option is to use a superimposed image comprising a number of pixels, such as an array of M×N pixels, each of said pixels having a color representing the type of contribution of the individual signal types in this superposition of the three absolute values. To give a distinct example, the absolute value for the absorption intensity is encoded in the color RED, the absolute value for the phase contrast intensity is encoded in the color BLUE and the absolute value for the scattering intensity is encoded in the color GREEN. While superposing now these intensity values for each pixel, the resulting image is rather easy to be interpreted. For example, regions in the image showing strong contribution from absorption and phase contrast are displayed consequentially in purpur or magenta colors. Regions showing strong contribution from phase contrast and scattering are displayed substantially in yellowish colors. In this example, the RGB color image can display the ratios of the three absolute values in a single image.

In another preferred embodiment according to the present invention, the scanning approach with a continuous movement of the object (probe), such as a structural body of any shape or a luggage, can be implemented advantageously, when the grating structure in the at least one analyzer grating comprises a number of sub-gratings having a shift perpendicular to the grating lines by an integer multiple of $p_2/n$, wherein $p_2$ is the period of the at least one analyzer grating and n is the number of the line detectors. According to the number of line detectors used, any point of the probe will be imaged n-times and the n-recorded intensities represent a phase stepping scan of the probe for this distinct point.

In order to avoid an undesired attenuation of the measured intensities due to bigger sizes of the probe and the optical alignment of the set-up, each of the sub-gratings can be disposed equidistantly from the x-ray source, wherein conveyor means are provided to move the object along a deflected trajectory following a shape given by the position of the sub-gratings. One preferred example for this arrangement comprises to dispose the adjacent sub-gratings on a circular arc trajectory having substantially a constant radius from the x-ray source. Therefore, the conveyor for the probe has to follow this circular trajectory as well as to guarantee an optimal vicinity to the diffractive and/or the analyzer grating.

BRIEF DESCRIPTION OF THE SEVERAL
VIEWS OF THE DRAWING

Preferred examples of the present invention are explained in detail below with reference to the attached drawings wherein.

DESCRIPTION OF THE INVENTION

Figure 1:
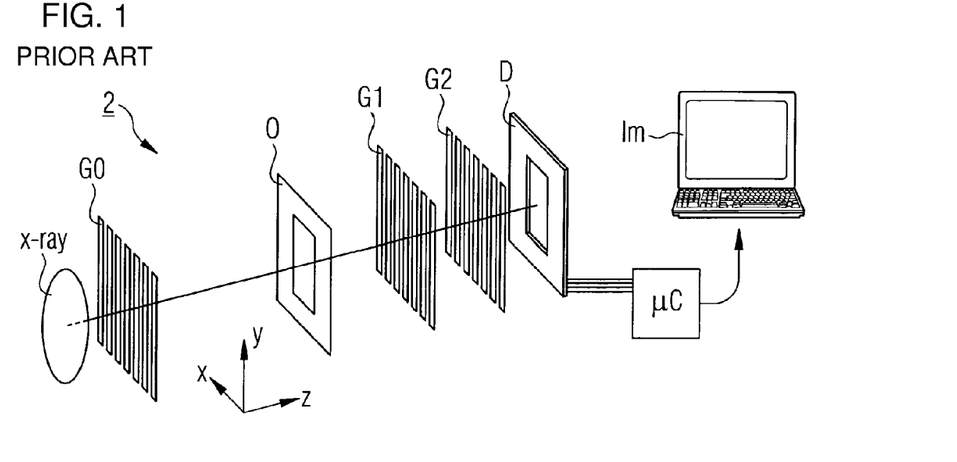
FIG. 1 depicts a simplified schematic view on the interferometer set-up.
Figure 2A:
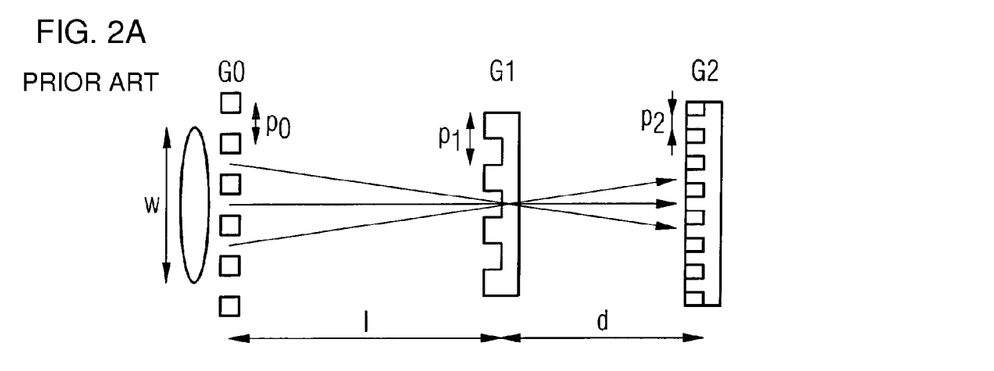
FIG. 2 illustrates a schematic view of a two grating interferometer (a) and the principles of the differential phase contrast image formation.
Figure 2B:
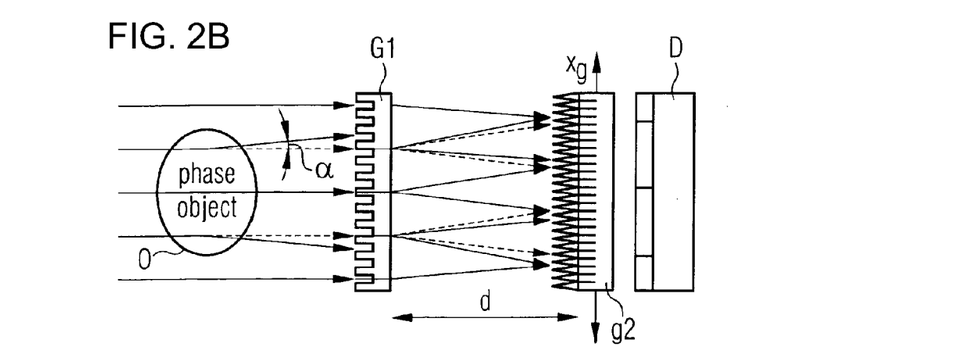

Since FIGS. 1 and 2a) have been described above to identify the content of the older European patent application 05 012 121, the focus is now shifted to the solutions according to the present invention to separate the absorption, differential phase contrast, and scattering signal caused by the sample from other effects, such as inhomogeneous illumination or imperfections of the gratings. In the context of this application, a so-called phase-stepping approach is used. While scanning one of the gratings (G2) along the transverse direction $x_g$ (see FIG. 2b), a series of images is recorded. The intensity signal I(m,n) in each pixel (m,n) in the plane of the detector D oscillates as a function of $x_g$ [FIG. 3]. These oscillations can be analyzed by several methods using an evaluation algorithm performed on evaluations means μC. Examples are parameter based sine fitting routines, one-dimensional auto-correlation analysis, or analytical approaches based on trigonometric equations in the case of only a few points. Also appropriate is the use of a numerical expansion (discrete fast Fourier Transform) of the intensity variations recorded in each detector pixel (m,n) in a Fourier series as $$I(m,n,x_g) = \Sigma a_i(m,n) \sin(k x_g + \Phi_i(m,n)) \approx a_0(m,n) + a_1(m,n) \sin(k x_g + \Phi_1(m,n)) + \ldots, \quad (1)$$

where $a_i$ are the amplitude coefficients and $\Phi_i$ the corresponding phase coefficients of the discrete Fourier transform, and $k = 2\pi/p_2$. The average transmission T(m,n) of the sample in each detector pixel is then given by $$T(m,n) = a^s_0(m,n)/a^r_0(m,n), \quad (2)$$

where the superscripts $^s$ and $^r$ denote the values measured with the sample in place ($^s$) and without the sample (reference: $^r$) T(m,n) is related to the average absorption in each pixel, A(m,n), by A(m,n)=1−T(m,n). Note that A(m,n) is identical to what would be measured without the interferometer in place. The component of the gradient of the object's integrated phase shift in the direction perpendicular to the lines in the gratings G1 and G2, the differential phase contrast (DPC) signal, dΦ(m,n)/dx, is related to the horizontal shift of the interference pattern measured in a phase stepping scan by $$d\Phi(m,n)/dx = \lambda d/p_2(\Phi^s(m,n) - \Phi^r(m,n)). \quad (3)$$

As already described in the previously filed European patent application, the differential signal can be integrated along x to yield the total phase shift of the object along the x-ray beam, when it traverses the object.

The new aspect and particular focus here is the evaluation of the amplitude of the intensity oscillation, $a_1$, in $I(m,n,x_g)$ [Eq. (1)]. The normalized oscillation amplitude, or the visibility of the interferometer is given by the ratio $a_1/a_0$. Without the sample in place this quantity contains information about the maximum contrast which is produced by the interferometer. It depends on the angular size of the X-ray source (transverse coherence) in the direction perpendicular to the grating lines, the quality of the gratings, and the energy spectrum of the X-ray source. Importantly, the value of the visibility can be changed by the interaction of the x-ray beam with the sample O. One of the interactions which can decrease the visibility is small angle scattering in the sample. Small angle scattering is particularly sensitive to density variations in the object on the length scale of several nanometers to micrometers. It naturally complements and extends the length scales which can be imaged directly by the method into the sub micrometer range. Although the information is ensemble averaged over a momentum transfer range which corresponds to the size of one detector pixel, the information can be very useful for detecting, e.g., pathologies like tumor structures. For higher energies (>30 keV), the Compton scattering increases significantly and is an additional source of scattering which yields important information about the internal structure of the sample O. The relative decrease of the visibility due to the x-ray scattering in the sample O can be quantified for each pixel (m,n) by defining the normalized visibility:

$$V(m,n) = V^s(m,n)/V^r(m,n) = [a^s_1(m,n)/a^s_0(m,n)]/[a^r_1(m,n)/a^r_0(m,n)]. \quad (4)$$

More precisely, a decrease of the V(m,n) due to the presence of the sample in the beam can be explained by considering the modification of the original coherence function of the x-ray beam. In such a picture, the scattering in the sample can be viewed as a second, larger, source with a correspondingly smaller transverse coherence length. A smaller coherence length effectively reduces the visibility in a phase stepping scan, and that is what is described with Eq. (4). The scattering signal (sometimes also referred to as the de-coherence signal) S is defined as $$S(m,n) = 1 - V(m,n). \quad (5)$$

For homogeneous samples, i.e. for samples with negligible small angle x-ray scattering (SAXS) or Compton scattering contributions, S(m,n)=0. Larger values of S, on the other hand, reflect a high amount of SAXS or Compton scattering in the sample and could yield information about its internal substructure.

Figure 3A:
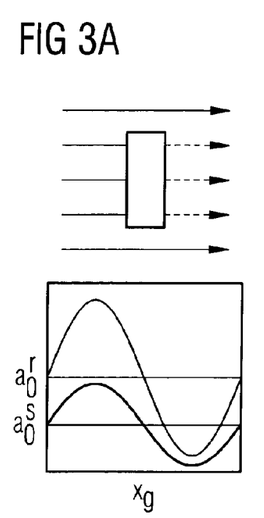
FIG. 3 illustrates an intensity variation in an individual detector pixel as a function of the grating position $x_g$ during a phase-stepping scan for (a) a pure absorption object, (b) a pure phase object with a linear phase gradient and (c) a pure scattering object.
Figure 3B:
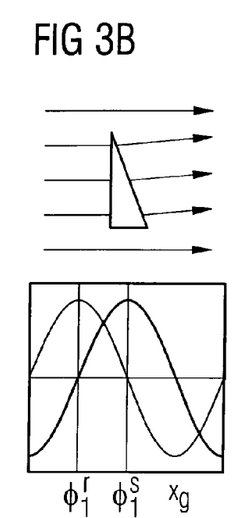
Figure 3C:
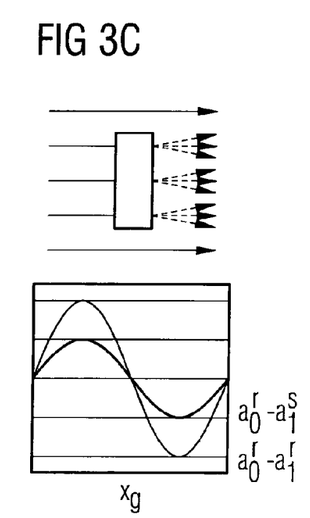

In FIG. 3, the three signals and their effects on the intensity curves, $I(m,n,x_g)$, during a phase stepping scan are shown. Depicted are the expected idealized intensity variations during a phase-stepping scan for a purely absorbing [FIG. 3(a)], a purely phase-shifting [FIG. 3(b)] and a purely scattering sample [FIG. 3(c)]. Real samples may, of course, produce signals in all three imaging channels. It turned out that it is the ratio of the different imaging signals which can help to identify different sample compositions more easily than based on a single imaging channel.

Some experimental results for a chicken wing have been received. The experiments were carried out on a Seifert ID 3000 x-ray generator operated at 35 kV/30 mA. A conventional tungsten (W) line focus tube (DX-W8×0.4-L) with a focus size of 8 (hor.)×0.4 (ver.) mm² was used. Due to an inclination of the target with respect to the optical axis of the setup of 6 degree, the effective source size was 0.8 (hor.)×0.4 (ver.) mm². The gratings G0, G1, G2 were fabricated by a process involving photolithography, deep etching into silicon and electroplating of gold. They had periods of: $p_0$=73 μm, $p_1$=3.9 μm, and $p_2$=2.0 μm. The height of the grating structures were 42 μm (G0), 35 μm (G1), and 26 μm (G2). The distances between the gratings were l=1.57 m and d=43 mm. The images were recorded using a 150 μm micron thick Cesium Iodide (CsI) scintillation screen with a demagnifying optical lens system and a cooled charge coupled device (CCD: Fingerlakes Instruments, FLI IMG 1001, KODAK chip with 1024×1024 pixels, 24×24 μm² pixel size). The effective spatial resolution was mainly determined by the thickness of the scintillation screen to ~0.1 mm.

The transmission T shows only a low transmission for the highly absorbing bone structures and a higher transmission in the surrounding tissue matrix. As expected, the phase contrast signal dΦ/dx enhances high frequency components of the image, e.g. the bone edges, and shows fine details in the soft tissue structure. The scattering image, S(m,n), shows relatively high values only for the bone structures, whereas the tissue is only present as a very faint signal. This observation suggests that the tissue structure can be considered as a relatively small source of SAXS, with very little density variations in the few micron length scale range, where the scattering signal is most effectively measured with the setup. The high density variations, particularly on the few micrometer and submicron length scale, produce a strong SAXS signal, which is reflected as an increase of the scattering signal. These first results suggest that the scattering image can offer a higher image contrast, particularly in the case, when constituents with different density variations on the few micron and submicron length scales are present.

Figure 4:
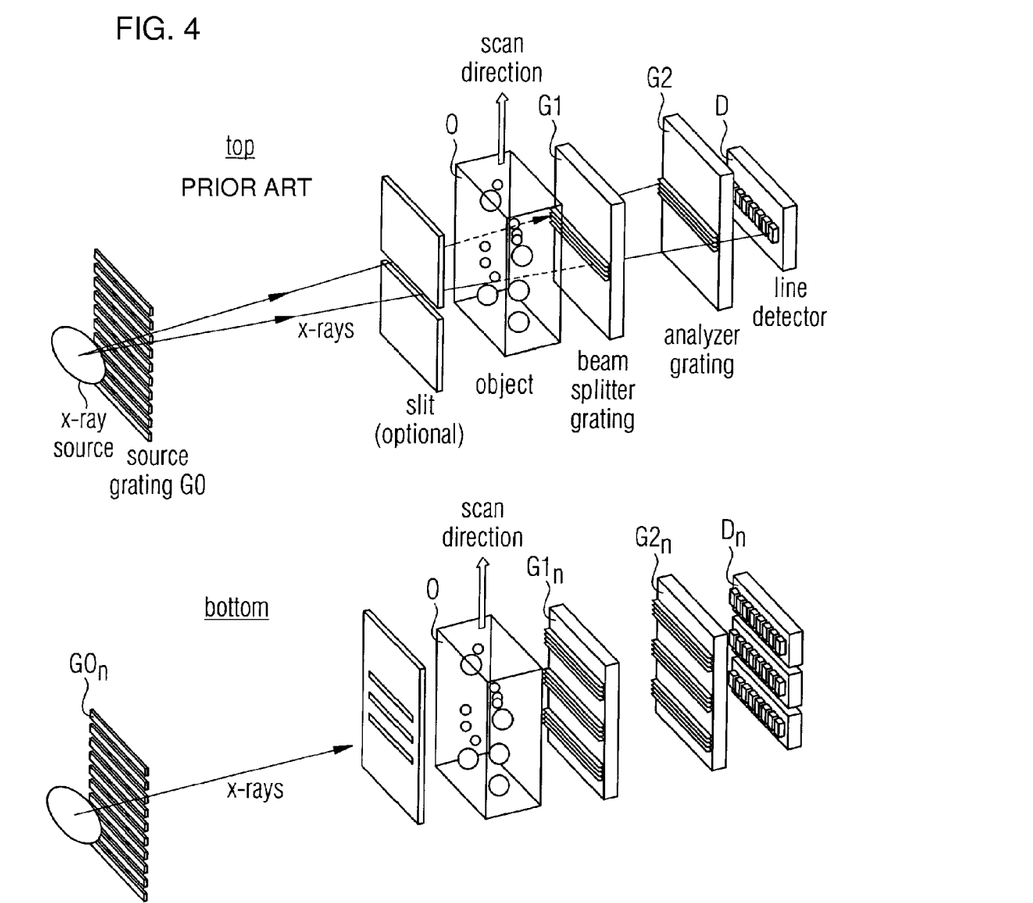
FIG. 4 depicts a schematic set-up of the interferometer for phase scanning as disclosed in the European patent application 05 012 121 (top) and a schematic set-up of the interferometer for phase scanning with an object continuously moved in the scanning direction.

This scattering signal yields improved contrast, particularly in the following applications:

1. Medical Imaging I:

It is known that the SAXS behavior of tumors can be significantly different from that of healthy tissue. This is because the growth of tumor tissue induces a density fluctuation on the micron and submicron scale which is different to that of healthy tissue. The scattering signal can thus be used to obtain a selectivity for different types of tissue even when the amplitude or phase contrast signals are identical what represents a remarkable progress over the signals interpretation facilities known so far;

2. Medical Imaging II:

Improved detection of structures on the order of the pixel size or smaller due to their scattering contribution (e.g. small bone fragments in a tissue matrix) are possible using the scattering signal. For example, it has been observed in bone samples [FIG. 4], that the scattering signal can be stronger than the amplitude contrast, as the hollow, porous bone structure gives rise to increased scattering;

3. Non-Destructive Testing I:

The scattering signal can be used for improved detection of micro-cracks, inclusions, or defects in objects. A specific application could be the detection of pollutions in food products, e.g. residual bone fragments in chicken fillets. In absorption contrast, this is difficult to detect, as the irregular shape of the samples dominates the differences in absorption;

4. Homeland Security:

Another interesting application with high potential for a commercial impact could be the screening of luggage for home land security applications, i.e. searching for explosives or illegal drugs.

The proposed three different signal channels, absorption, phase shift, and scattering, are difficult to display, as this requires the exact comparison of several (grey tone) images, and sometimes small differences in the ratios of the three channels are of interest. The conclusion according to the present invention is to facilitate this comparison by displaying two or all three signal channels in color codes, i.e. attributing each channel to a different color, e.g. to red, green, and blue in an RGB color image. This way the ratios of the signal channels can be displayed in a single image. Several possibilities of assigning the different channels of an RGB image can be implemented. Unfortunately, in patent applications figures are only allowed to be presented as grey tone images. However, the persons skilled in the art have a basic understanding of the color mixing principles according to the colored triangle.

The grating based phase contrast method detects phase gradients, the phase needs to be retrieved by integration of the differential phase signal. The absorption image and the scattering image are not differential images. As sometimes the phase retrieval by integration is difficult and results in artifacts, it can instead be useful to differentiate the absorption and scattering images (which usually causes less artifacts), and to display the three differential images—preferentially in color encoding as described above.

In the previously filed European patent application 05 012 121, the possibility of using the method in x-ray scanners, with a fan beam defined by a narrow slit and a line detector has been addressed. Indeed, such scanning systems have substantial advantages over full-field x-ray imaging systems:

1. The system only requires a line detector, which costs significantly less compared to a two-dimensional detector.
2. It is much easier (and cheaper) to obtain line detectors with very high sensitivity and low noise. Single photon counting line detectors are commercially available.
3. The set-up suppresses blurring or decreased contrast of the image by scattered x-rays (Compton scattering) and does not require an anti-scatter grid.

However, it is complicated and time consuming to perform a nested scanning scheme—for the phase stepping in each image line and for the acquisition of a two-dimensional image. Moreover, in some applications, e.g. the investigation of products or luggage on a continuously moving conveyer belt, the phase stepping would require stopping the conveyer motion during the time needed for the phase stepping scan, and this is often not easily possible. In the FIG. 8, an efficient method to perform a nested scan efficiently is depicted. The upper part shows the scanning setup already described previously in the submitted patent with a single line detector. The lower setup comprises an array of n line detectors $D_n$ (only three are shown for simplicity). The essential feature is that each of the sub-gratings $G2_n$ in G2 are slightly shifted in their position perpendicular to the grating lines. This shift between two neighboring sub-gratings $G2_n$ should be an integer multiple of $p_2/n$. The line detectors $D_n$ are continuously read out, while the sample is moving along the scan direction (e.g. $x_g$ as shown in FIG. 3). A certain point in the sample will thus be imaged n times, once by each line detector $D_n$, and the n recorded intensities represent a phase stepping scan for this point. Thus, the number n of line detectors results in n points along the phase stepping on this point. Because the recording of these intensities is done for n different positions of the sample, i.e. at different times, the image data of the n line detectors need to be rearranged accordingly for the display on the display means Im. A continuous motion of the sample O is possible. An additional advantage of this setup is the fact that n times more flux is recorded compared to a setup with a single line detector as described previously.

Figure 5A:
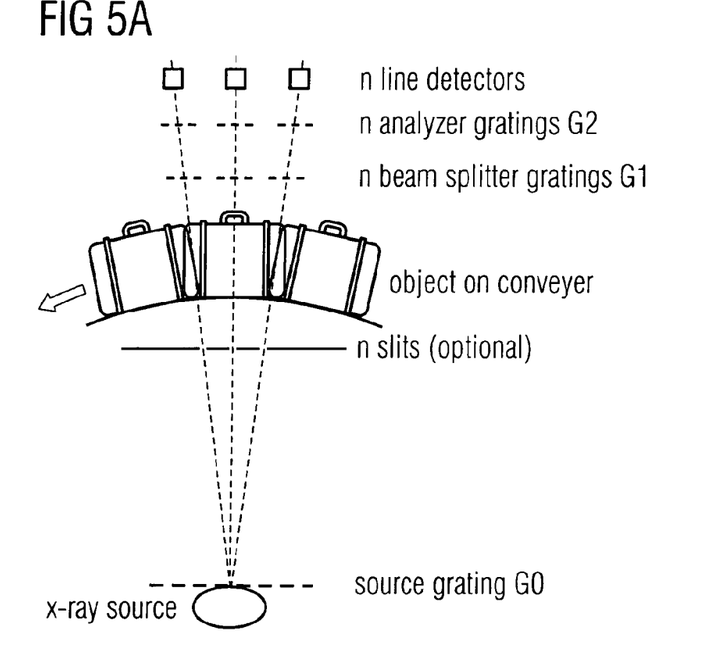
FIG. 5 a schematic view on two possible set-ups for the phase scanning approach of continuously moved objects.
Figure 5B:
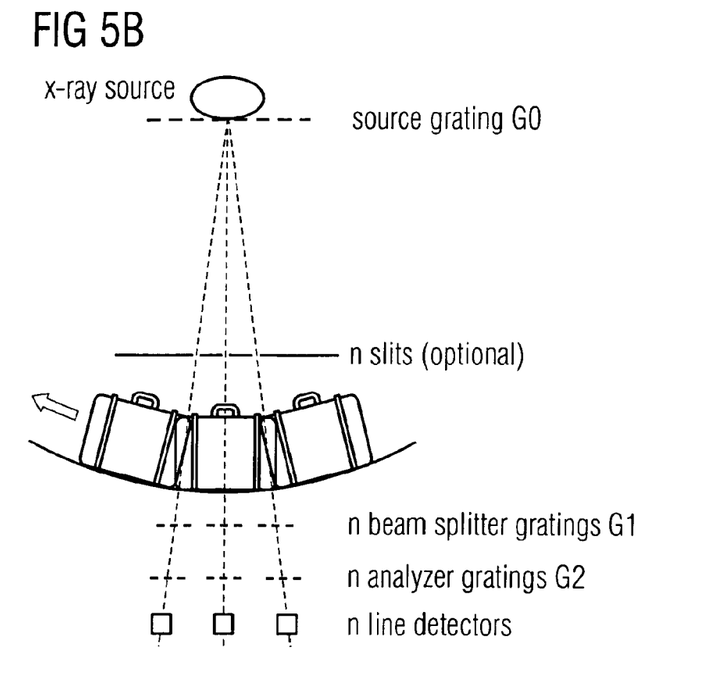

In order to avoid an undesired attenuation of the measured intensities due to bigger sizes of the probe O and the optical alignment of the set-up, each of the sub-gratings $G2_n$ can disposed equidistantly from the x-ray source, wherein conveyor means are provided to move the object along a deflected trajectory following a shape given by the position of the sub-gratings $G2_n$ as this is shown in FIGS. 5A and 5B. The preferred examples for this arrangement comprise to dispose the adjacent sub-gratings on a circular arc trajectory having substantially a constant radius from the x-ray source or on an even level being arranged to allow a radial throughput of the x-rays that penetrated the probe which is shown in FIGS. 5A and 5B. Therefore, the conveyor for the probe, i.e. a luggage, has to follow this circular trajectory as well as to guarantee an optimal vicinity to the diffractive and/or the analyzer grating.

The invention claimed is:

1. An interferometer for x-rays for obtaining quantitative x-ray images from an object, comprising:
   a) an x-ray source;
   b) a diffractive beam splitter grating other than a Bragg crystal;
   c) a position-sensitive detector with spatially modulated detection sensitivity having a plurality of individual pixels;
   d) a recording device for recording images from said detector; and
   e) an evaluating device for evaluating respective intensities for each pixel in a series of the images in order to identify a characteristic of the object for each individual pixel as an absorption-dominated pixel and/or a differential phase contrast-dominated pixel and/or an x-ray scattering-dominated pixel;
   f) means for generating display data for displaying the evaluated images of the object, wherein an encoding approach is used for differentiating an individual contribution to each individual pixel, and wherein:
      a value of a differential absorption signal $dA(m,n)/dx$ or an absorption signal $dA(m,n)$ or an absolute value of any of the differential absorption signal or the absorption signal $dA(m,n)$ is assigned to a first codification;
      a value of a differential phase contrast signal $d\phi(m,n)/dx$ or an integrated phase signal $\phi(m,n)$ or an absolute value of any of the differential phase contrast signal $d\phi(m,n)/dx$ or the integrated phase signal $\phi(m,n)$ is assigned to a second codification; and
      a value of a differential scattering signal $dS(m,n)/dx$ or a scattering signal $S(m,n)$ or an absolute value of any of the differential scattering signal $dS(m,n)/dx$ or the scattering signal $S(m,n)$ is assigned to a third codification.

2. The interferometer according to claim 1, wherein said x-ray source is a standard polychromatic x-ray source.

3. The interferometer according to claim 1, wherein said beam splitter grating is in transmission geometry.

4. The interferometer according to claim 1, wherein said evaluating device comprises calculation means for analyzing a course of detected intensities for each pixel of the detector, wherein the course of the detected intensities is yielded by a predetermined number of the images recorded in step d).

5. The interferometer according to claim 4, wherein said calculation means includes a memory for storing the images without an object being placed in an x-ray beam line.

6. The interferometer according to claim 1, which comprises an analyzer grating for generating the spatially modulated detection sensitivity, said analyzer grating having absorbing lines at a same periodicity and orientation as a set of fringes generated by said diffractive beam splitter grating, and wherein said analyzer grating is placed in a plane of said detector.

7. The interferometer according to claim 6, wherein said analyzer grating is placed immediately in front of said detector.

8. The interferometer according to claim 6, wherein said phase-stepping approach is achieved by scanning at least one of said gratings relative to the object in a direction substantially perpendicular to the orientation of the lines in said at least one of said gratings.

9. The interferometer according to claim 1, wherein said means for generating display data are programmed to calculate a superimposed image containing all three values being superimposed according to a respective codification thereof.

10. The interferometer according to claim 1, wherein said means for generating display data are configured to display an individual image for each of the three codifications.

11. The interferometer according to claim 1, wherein each of the three codifications comprises an individual signal type selected from the group consisting of an individual letter, a symbol, and/or a color.

12. The interferometer according to claim 1, wherein a superimposed image comprises an array of M×N pixels, each of the pixels having a color representing a type of contribution of individual signal types in a superposition of the three absolute values.

13. The interferometer according to claim 1, configured for processing hard x-rays.

14. An interferometer for x-rays for obtaining quantitative x-ray images from an object, comprising:
   a) a slit mask having a given number of slits arranged between an X-ray source and a beam splitter grating, allowing the object to be disposed between said slit mask and said beam splitter grating;
   b) at least one analyzer grating disposed between said beam splitter grating and a detector, wherein said beam splitter grating and each of said at least one analyzer grating have a grating structure associated with the given number of slits in said slit mask;
   c) wherein said detector is configured as an array of individual line detectors each having a number of pixels, and wherein a number of said line detectors corresponds to the given number of slits in said slit mask;
   d) means for moving the object along a scan direction oriented perpendicular to an orientation of the gratings in said grating structure;
   e) means for recording the images from said detector in a continuous scanning approach; and
   f) means for evaluating intensities for each pixel in a series of the images representing a phase stepping scan for at least a part of the object being moved along the scan direction;
   wherein the grating structure in said at least one analyzer grating comprises a number of sub-gratings having a shift perpendicular to grating lines by an integer multiple of $p_2/n$, wherein $p_2$ is a period of said at least one analyzer grating and n is a given number of said line detectors.

15. The interferometer according to claim 14, configured for processing hard x-rays.

16. An interferometer for x-rays for obtaining quantitative x-ray images from an object, comprising:
   a) a slit mask having a given number of slits arranged between an X-ray source and a beam splitter grating, allowing the object to be disposed between said slit mask and said beam splitter grating;
   b) at least one analyzer grating disposed between said beam splitter grating and a detector, wherein said beam splitter grating and each of said at least one analyzer grating have a grating structure associated with the given number of slits in said slit mask;
   c) wherein said detector is configured as an array of individual line detectors each having a number of pixels, and wherein a number of said line detectors corresponds to the given number of slits in said slit mask;
d) means for moving the object along a scan direction oriented perpendicular to an orientation of the gratings in said grating structure;
e) means for recording the images from said detector in a continuous scanning approach; and
f) means for evaluating the intensities for each pixel in a series of the images representing a phase stepping scan for at least a part of the object being moved along the scan direction;

wherein sub-gratings are disposed equidistantly from said x-ray source, and wherein conveyor means are provided for moving the object along a deflected trajectory following a shape defined by a position of said sub-gratings.

* * * * *